(12) United States Patent
Mohammed et al.

(10) Patent No.: US 11,166,889 B2
(45) Date of Patent: Nov. 9, 2021

(54) COMPOSITIONS COMPRISING PH-SENSITIVE MICROCAPSULES

(71) Applicant: Colgate-Palmolive Company, New York, NY (US)

(72) Inventors: Evelyn Mohammed, Hillsborough, NJ (US); Amjad Farooq, Hillsborough, NJ (US); Robert Vogt, Princeton Junction, NJ (US); Paul Thomson, Piscatatway, NJ (US); Yelloji-Rao Mirajkar, Piscataway, NJ (US); Victoria Yeung, Livingston, NJ (US)

(73) Assignee: Colgate-Palmolive Company, New York, NY (US)

( * ) Notice: Subject to any disclaimer, the term of this patent is extended or adjusted under 35 U.S.C. 154(b) by 563 days.

(21) Appl. No.: 15/756,603

(22) PCT Filed: Dec. 13, 2017

(86) PCT No.: PCT/US2017/066081
§ 371 (c)(1),
(2) Date: Mar. 1, 2018

(87) PCT Pub. No.: WO2019/117890
PCT Pub. Date: Jun. 20, 2019

(65) Prior Publication Data
US 2020/0237629 A1    Jul. 30, 2020

(51) Int. Cl.
| | | |
|---|---|---|
| *A61K 8/11* | (2006.01) | |
| *A61K 8/21* | (2006.01) | |
| *A61K 8/73* | (2006.01) | |
| *A61K 8/81* | (2006.01) | |
| *A61K 8/25* | (2006.01) | |
| *A61K 8/92* | (2006.01) | |
| *A61Q 11/00* | (2006.01) | |

(52) U.S. Cl.
CPC ............... *A61K 8/11* (2013.01); *A61K 8/21* (2013.01); *A61K 8/25* (2013.01); *A61K 8/731* (2013.01); *A61K 8/8152* (2013.01); *A61K 8/927* (2013.01); *A61Q 11/00* (2013.01); *A61K 2800/412* (2013.01)

(58) Field of Classification Search
CPC .......... A61K 8/927; A61K 8/25; A61K 8/731; A61K 2800/412; A61K 8/8152; A61K 8/21; A61K 8/11; A61Q 11/00
See application file for complete search history.

(56) References Cited

U.S. PATENT DOCUMENTS

| | | | |
|---|---|---|---|
| 4,071,614 A * | 1/1978 | Grimm, III | ............... A61K 8/11 424/10.32 |
| 6,022,501 A | 2/2000 | Dexter et al. | |
| 7,763,235 B2 | 7/2010 | Boyd et al. | |
| 8,178,483 B2 | 5/2012 | Masters et al. | |
| 8,540,823 B2 | 9/2013 | Drehs et al. | |
| 2004/0062778 A1* | 4/2004 | Shefer | ................... A61K 9/2013 424/400 |
| 2004/0161438 A1 | 8/2004 | Jungmann et al. | |
| 2007/0259170 A1 | 11/2007 | Brown et al. | |
| 2008/0014393 A1* | 1/2008 | Denome | ............... C11D 17/042 428/35.7 |
| 2008/0260836 A1 | 10/2008 | Boyd | |
| 2010/0251485 A1 | 10/2010 | Smets et al. | |
| 2011/0171349 A1* | 7/2011 | Poortinga | ............. A61K 9/5089 426/61 |
| 2011/0268778 A1* | 11/2011 | Dihora | ..................... A61K 8/11 424/401 |
| 2012/0258175 A1 | 10/2012 | Murthy et al. | |
| 2013/0017612 A1 | 1/2013 | Li et al. | |
| 2014/0031463 A1 | 1/2014 | Kempter et al. | |
| 2014/0249066 A1 | 9/2014 | Meek et al. | |

FOREIGN PATENT DOCUMENTS

| | | |
|---|---|---|
| EP | 1449509 | 8/2004 |
| EP | 2687287 | 1/2014 |
| JP | 2017-114802 A | 6/2017 |
| WO | 2006/047872 | 5/2006 |
| WO | WO 2007/130685 | 11/2007 |
| WO | 2008/121518 | 10/2008 |
| WO | 2017/036542 | 3/2017 |

OTHER PUBLICATIONS

International Search Report and Written Opinion of the International Searching Authority in International Application No. PCT/US2017/066081, dated Aug. 13, 2018.

Ahmed, A.R. et al., "Chapter 3—Aqueous polymeric coatings: New opportunities in drug delivery systems" in Drug Delivery Aspects vol. 4: Expectation and Realities of Multifunctional Drug Delivery Systems, Edited by Shegokar, R., Elsevier, ISBN 978-0-12-821222-6, (2020), pp. 33-56.

Dash Z. et al., "Release Kinetic Studies of Aspirin Microcapsules from Ethyl Cellulose Acetate Phthalate and their Mixtures by Emulsion Solvent Evaporation Method", Sci Pharm. (2010), vol. 78, pp. 93-101.

Rogers, T. L. and Wallick, D., "Reviewing the use of ethylcellulose, methylcellulose and hypromellose in microencapsulation. Part 3: Applications for microcapsules", Drug Development and Industrial Pharmacy (2012), vol. 38, pp. 521-539.

* cited by examiner

Primary Examiner — Jianfeng Song

(57) ABSTRACT

Disclosed herein is a composition comprising a pH-sensitive microcapsule comprising (1) a shell wall comprising at least one polymer chosen from cellulose derivatives and acrylate derivatives, and at least one structuring agent chosen from shellac, ethyl cellulose, and fumed silica, and (2) at least one functional ingredient encapsulated inside the shell wall; and a carrier having a pH of less than about 7. Further disclosed herein are methods of making a composition comprising a pH-sensitive microcapsule.

11 Claims, No Drawings

COMPOSITIONS COMPRISING PH-SENSITIVE MICROCAPSULES

BACKGROUND

Compositions such as oral care compositions, personal care compositions, and home care compositions are used for a wide variety of purposes, including the enhancement of personal health, hygiene, and appearance; preventing or treating a variety of diseases and other conditions in mammals, and delivery of agents to household surfaces for cleaning, disinfecting, imparting pleasant odors, and other benefits. Such compositions may contain films or delivery agents that have functional ingredients contained therein, and that may be stored in a carrier or vehicle of the product. Upon use, the films or delivery agents may degrade by chemical or physical disruption, thereby releasing the functional ingredients into the surrounding environment. In this manner, the films and delivery agents may provide an opportunity for localized release of high concentration of functional ingredients near a target surface and/or controlled timing of release of the functional ingredients.

There is still an ongoing need, however, for improved stability and efficacy in such compositions, as well as the achievement of targeted, sustained and/or controlled release of functional ingredients. Other problems remain with regard to incompatibility of various components in a formulation. For example, organic acids have been found to make some oral care compositions unstable by impacting the solubility or precipitation of polymers, thus leading to overly soluble and unstable films. Additionally, larger-sized delivery agents may be more difficult to suspend in a composition, and/or may have a tendency to settle out of the composition, reducing their effectiveness. These kinds of disadvantage can lead to undesirable instability problems in all realms of consumer products.

Additionally, although such products have met with consumer approval, the art seeks to further improve aesthetic effects as well as cosmetic and therapeutic benefits of these products so as to encourage the use of these products, such as the use of dentifrices in practicing oral hygiene. Therefore, there is an ongoing need for improved delivery agents having beneficial properties such as increased stability, optimal adhesion to the target surface, optimal timing of delivery, and release of higher concentrations of functional ingredients, as well as methods for improving the aesthetics of oral, personal, and home care compositions comprising delivery agents for the release of functional ingredients.

The compositions and methods disclosed herein provide superior ability to release functional ingredients, based on the discovery that including or providing a pH-sensitive microcapsule that is soluble above a threshold pH results in compositions that are able to provide a desirable rate, amount and time of release of the functional ingredient. The compositions disclosed herein are advantageous in that they exhibit benefits such as enhanced stability and delivery profiles for compositions, such as oral care, personal care, and home care compositions, as well as pH-microcapsules that are capable of being adequately suspended in a composition.

BRIEF SUMMARY

Disclosed herein are compositions comprising at least one pH-sensitive microcapsule comprising (1) a shell wall comprising at least one polymer chosen from cellulose derivatives and acrylate derivatives, and at least one structuring agent chosen from shellac, ethyl cellulose, and fumed silica, and (2) at least one functional ingredient encapsulated inside the shell wall; and a carrier having a pH of less than about 6. In certain embodiments, the compositions disclosed herein may be chosen from oral care compositions, personal care compositions, and home care compositions.

In various embodiments of the disclosure, the cellulose derivative is chosen from at least one of hydroxypropyl methyl cellulose phthalate and hydroxypropyl methyl cellulose acetate succinate, and in certain embodiments, the acrylate derivative is an acrylates/$C_{1-2}$ succinates/hydroxyacrylates copolymer. In certain embodiments, the at least one structuring agent is shellac. In certain embodiments, the at least one acrylate derivative is an acrylates/$C_{1-2}$ succinates/hydroxyacrylates copolymer and the at least one structuring agent is shellac.

In certain embodiments disclosed herein, the shell wall further comprises at least one of anionic copolymers based on methacrylic acid and methyl methacrylate, hydroxypropyl cellulose, polyvinyl alcohol, and polyvinyl alcohol-polyethylene glycol. In various embodiments, the shell wall has a thickness ranging from about 10 µm to about 30 µm, such as about 12 µm to about 26 µm. In certain embodiments, the at least one pH-sensitive microcapsule has a mean diameter ranging from about 25 µm to about 75 µm, such as from about 40 µm to about 50 µm.

In certain embodiments disclosed herein, the ratio of the at least one polymer and the at least one structuring agent is at least about 1:7, such as at least about 1:10, by weight based on the total weight of the shell wall. In certain other embodiments disclosed herein, the ratio of the at least one of anionic copolymers based on methacrylic acid and methyl methacrylate, hydroxypropyl cellulose, polyvinyl alcohol, and polyvinyl alcohol-polyethylene glycol to the at least one polymer to the at least one structuring agent is at least about 0.05:1:7, such as at least about 0.1:1:7, by weight based on the total weight of the shell wall. In other embodiments disclosed herein, the ratio of the at least one of anionic copolymers based on methacrylic acid and methyl methacrylate, hydroxypropyl cellulose, polyvinyl alcohol, and polyvinyl alcohol-polyethylene glycol to the at least one polymer to the at least one structuring agent is at least about 0.05:1:10, such as at least about 0.1:1:10, by weight based on the total weight of the shell wall.

In certain embodiments disclosed herein, the at least one polymer is present in the shell well in an amount ranging from about 5% to about 15%, by weight based on the total weight of the at least one pH-sensitive microcapsule, and in certain embodiments disclosed herein, the at least one structuring agent is present in the shell wall in an amount ranging from about 85% to about 95%, by weight based on the total weight of the at least one pH-sensitive microcapsule. In certain embodiments, the at least one of anionic copolymers based on methacrylic acid and methyl methacrylate, hydroxypropyl cellulose, polyvinyl alcohol, and polyvinyl alcohol-polyethylene glycol is present in the shell wall in an amount ranging from about 0.5% to about 2%, by weight based on the total weight of the at least one pH-sensitive microcapsule.

According to various embodiments of the disclosure, the at least one functional ingredient is chosen from flavorants, fragrances, essential oils, emulsifying agents, thickening agents, colorants, cooling agents, sweeteners, binding agents, sulfur precipitating agents, plasticizing agents, pharmaceutical actives, salivary stimulants, stain preventative agents, anti-microbial agents, anticaries agents, anticalculus agents, antiplaque agents, periodontal actives, breath-freshening agents, malodor control agents, whitening agents, vitamins, herbs and herbal extracts, amino acids, enzymes and other proteins, steroids, anti-inflammatory agents, abrasives, antiperspirant actives, deodorant actives, conditioning agents, moisturizers, emollients, sunscreens, sunblocks, alcohols, denaturants, anti-dandruff agents, anticholinergics, anesthetics, foaming agents, surfactants, cleansing agents, bleaches, detergents, fabric softening agents, and preservatives. In certain embodiments, at least one functional ingredient is encapsulated inside the shell wall in an amount ranging from about 4% to about 30%, such as from about 5% to about 15%, by weight based on the total weight of the at least one pH-sensitive microcapsule. In certain embodiments, the at least one functional ingredient is released from the pH-sensitive microcapsule when the pH of the composition decreases to a pH of less than about 6, such as less than about 6 or less than about 5.5, and in certain embodiments, the at least one functional ingredient remains encapsulated inside the shell wall for at least about 4 weeks, such as at least about 8 weeks, at least about 12 weeks, at least about 16 weeks, at least about 6 months, or at least about 1 year, when the composition is at room temperature. As use herein, "room temperature" may range from about 20° C. to about 25° C., such as about 22° C. or about 23° C. In other embodiments, the at least one functional ingredient remains encapsulated inside the shell wall for at least about 4 weeks, such as at least about 8 weeks, at least about 12 weeks, at least about 16 weeks, at least about 6 months, or at least about 1 year, when the composition is at a temperature of at least about 40° C.

Also disclosed herein are methods of making a composition comprising at least one pH-sensitive microcapsule, said method comprising (1) preparing at least one pH-sensitive microcapsule by spraying jetting a shell fluid comprising at least one polymer chosen from cellulose derivatives and acrylate derivatives and at least one structuring agent chosen from shellac, ethyl cellulose, and fumed silica around a core fluid comprising at least one functional ingredient, such that the shell fluid encapsulates the core fluid to produce at least one droplet; (2) solidifying the at least one droplet to produce at least one pH-sensitive microcapsule; and (3) the at least one pH-sensitive microcapsule with a carrier having a pH of less than about 6 to form a composition. In certain embodiments of the methods disclosed herein, the at least one pH-sensitive microcapsule has a mean diameter ranging from about 25 µm to about 75 µm, such as about 40 µm to about 50 µm.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/ B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, components, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith.

Unless otherwise specified, all percentages and amounts expressed herein and elsewhere in the specification should be understood to refer to percentages by weight. The amounts given are based on the active weight of the material. Unless otherwise specified, all component or composition amounts are in reference to the active amount of that component or composition, and exclude impurities or by-products, which may be present in commercially available sources.

All references cited herein are hereby incorporated by reference in their entireties. In the event of a conflict in a definition in the present disclosure and that of a cited reference, the present disclosure controls.

Disclosed herein are compositions comprising pH-sensitive microcapsules comprising a shell wall that encapsulates at least one functional ingredient. The pH-sensitive microcapsules disclosed herein are capable of delivering the at least one functional ingredient into a composition in which the pH-sensitive microcapsule is incorporated, such as oral care, personal care, and home care compositions. The pH-sensitive microcapsules disclosed herein are acid-stable, allowing for their stable incorporation into an acidic carrier, such as a carrier having a pH of less than about 6. When the composition comprising at least one pH-sensitive microcapsule is contacted with a more basic solution, such as water, including for example saliva, the overall pH of the composition is raised, causing the pH-sensitive microcapsule to disintegrate and release the at least one functional ingredient encapsulated within the shell wall.

As used herein, the term "microcapsules" refers to small particles, such as micron-sized particles, comprising a continuous shell wall of a film and an internal space capable of holding at least one functional ingredient. In certain embodiments, the microcapsules disclosed herein are stable in a composition having a pH ranging from about 1 to about 6, such as about 2 to about 6, about 3 to about 5, or about 5.6. The microcapsules disclosed herein may vary in size and shape. In certain embodiments, the microcapsules are approximately spherical and in certain embodiments the microcapsules are approximately ovoidal or irregularly shaped. In certain embodiments, the microcapsules may range in size from about 20 μm to about 100 μm, such as about 25 μm to about 75 μm, about 30 μm to about 60 μm, about 35 μm to about 50 μm, about 38 μm, or about 46 μm to about 47 μm.

In certain embodiments of the disclosure, the size of the pH-sensitive microcapsules in the composition may vary from each other, and in certain embodiments the size of the pH-sensitive microcapsules in a composition may be substantially the same. The size of the pH-sensitive microcapsules may be determined pursuant to any of a variety of criteria, including manufacturing convenience, effect on visual appearance, surface area, effect on texture in the composition, and combinations thereof. It is understood that in various embodiments comprising a plurality of microcapsules, the microcapsules may be present in a range of sizes due to a variety of factors, including random variation in size, manufacturing tolerances, and intentional sizing or mixing of the microcapsules during manufacture of the composition. As referred to herein, sizes refer to the mean size of microcapsules in a given plurality of microcapsules.

As used herein, the term "pH-sensitive" indicates that the stability of the shell wall of the microcapsules disclosed herein depends on the pH of the surrounding environment of the microcapsule, such as the pH of the carrier in the composition comprising the pH-sensitive microcapsule. Accordingly, the pH-sensitive microcapsules disclosed herein may be stored for extended periods of time in a surrounding environment having a pH of about 6 or less, such as about 5.7 or less or about 5.6 or less, or a pH ranging from about 1 to about 6. The pH-sensitive microcapsules may be stable in an acidic composition, such as a composition having a pH of less than about 6. In certain embodiments, the pH-microcapsules are stable for at least about 4 weeks, such as at least about 8 weeks, at least about 12 weeks, at least about 16 weeks, at least about 20 weeks, at least about 6 months, or at least about a year, in an acidic composition, such as a composition having a pH of less than about 6. In certain embodiments, the pH-microcapsules are stable at a temperature of at least about 40° C. for at least about 4 weeks, such as at least about 8 weeks, at least about 12 weeks, at least about 16 weeks, at least about 20 weeks, at least about 6 months, or at least about a year, in an acidic composition, such as a composition having a pH of less than about 6. For the purposes of this disclosure, it is assumed that aging a sample for 13 weeks at about 40° C. is similar to and simulates the aging of a sample for about one year at room temperature (e.g., one year of shelf life).

In certain embodiments, stability may be measured, for example, by comparing the amount of the at least one functional ingredient that has been leaked in a composition that has been aged for an amount of time. In certain embodiments, solid-phase microextraction (SPME) analysis may be conducted on a composition, and the resultant analytes analyzed, for example by gas chromatography/mass spectrometry, to determine the quantity of functional ingredient in a composition.

The pH-sensitive microcapsule is designed to disintegrate or dissolve when the composition is applied to a target area and/or diluted with water or other pH-increasing substance, with or without a mechanical agitation, such as stirring, rubbing or scrubbing.

In various embodiments disclosed herein, the pH-sensitive microcapsules comprise a shell wall comprising at least one polymer chosen from hydroxypropyl methylcellulose derivatives and acrylate derivatives and at least one structuring agent chosen from shellac, ethyl cellulose, and fumed silica. In certain embodiments, the shell wall may further comprise additional ingredients, such as, for example, at least one of anionic copolymers based on methacrylic acid and methyl methacrylate, hydroxypropyl cellulose, polyvinyl alcohol, and polyvinyl alcohol-polyethylene glycol. In certain embodiments, the at least one pH-sensitive microcapsule is incorporated into a carrier to create a composition.

In certain embodiments disclosed herein, the at least one polymer is a hydroxypropyl methylcellulose derivative. The hydroxypropyl methylcellulose derivative may be chosen, for example, from hydroxypropyl methylcellulose phthalate (HPMCP) and hydroxypropyl methylcellulose acetate succinate (HPMCAS).

In certain embodiments disclosed herein, the at least one polymer is an acrylate derivative. The acrylate derivative may be chosen, for example, from methacrylic acid, alkene succinic acid, and alkyl and hydroxyl alkyl esters of acrylates and methacrylates, such as acrylates/hydroxyesters acrylates (such as, for example, Acudyne® manufactured by the Dow Chemical Co.). In certain embodiments, the acrylate derivative is an acrylates/$C_{1-2}$ succinates/hydroxyacrylates copolymer.

According to various embodiments of the disclosure, the shell wall of the pH-microcapsule comprises at least one structuring agent chosen from shellac, ethyl cellulose, and fumed silica. In certain embodiments, the fumed silica may be Aerosil® fumed silica, manufactured by Evonik.

In certain embodiments, the shell wall of the pH-microcapsule further comprises at least one additional ingredient chosen from anionic copolymers based on methacrylic acid and methyl methacrylate, hydroxypropyl cellulose, polyvinyl alcohol, and polyvinyl alcohol-polyethylene glycol. In certain embodiments, the at least one structuring agent is shellac.

The at least one polymer and the at least one structuring agent may be present in the shell wall in a ratio of at least about 7:1 (structuring agent:polymer), such as at least about 10:1. In exemplary embodiments disclosed herein where the shell wall of the pH-microcapsule further comprises at least one additional ingredient, the additional ingredient may be present in the shell wall in a ratio of at least about 7:1:0.05 (structuring agent:polymer:additional ingredient), such as at least about 7:1:0.1, and in certain embodiments disclosed herein the additional ingredient may be present in the shell wall in a ratio of at least about 10:1:0.05 (structuring agent:polymer:additional ingredient), such as at least about 7:1:0.1.

In certain embodiments disclosed herein, the at least one polymer chosen from hydroxypropyl methylcellulose derivatives and acrylate derivatives may be present in the microcapsule shell wall in an amount ranging from about 5% to about 20%, such as from about 9% to about 15%, or about 10% to about 12%, by weight relative to the total weight of the microcapsule shell wall. In certain embodiments, the at least one structuring agent chosen from shellac, ethyl cellulose, and fumed silica may be present in the microcapsule shell wall in an amount ranging from about 80% to about 95%, such as from about 85% to about 92%, or about 86% to about 91%0, by weight relative to the total weight of the microcapsule shell wall. In certain embodiments the at least one additional ingredient chosen from anionic copolymers based on methacrylic acid and methyl methacrylate, hydroxypropyl cellulose, polyvinyl alcohol, and polyvinyl alcohol-polyethylene glycol is present in the microcapsule shell wall in an amount ranging from about 0.5% to about 2%, such as about 1%, by weight relative to the total weight of the microcapsule shell wall.

In various embodiments disclosed herein, the shell wall of the pH-sensitive microcapsules have a thickness ranging from about 12 μm to about 30 μm, such as about 15 μm to about 22 μm. In certain embodiments, shell wall of the pH-sensitive microcapsules has a thickness of about 13 μm, about 14 μm, about 15 μm, about 21.5 μm, about 22 μm, about 24 μm, about 25.5 μm, about 26 μm, or about 27 μm.

In certain embodiments, the at least one hydroxypropyl methylcellulose derivative and the at least one structuring agent form a film that encapsulates the at least one functional ingredient to form a microcapsule. As used herein, "film" refers to a material that may have substantially lamellar structure, or alternatively may have a substantially non-lamellar structure (e.g., a particle or bead). The at least one functional ingredient is released upon pH neutralization of the composition, such as by the addition of water, including saliva, wherein the shell wall becomes unstable and deteriorates.

In various embodiments, the pH-sensitive microcapsule disintegrates during use of the composition. In some embodiments, the microcapsule releases the at least one functional ingredient into a carrier. As referred to herein, "disintegrate" refers to physical disruption of the microcapsule, so as to produce microcapsule fragments of reduced size compared to the original microcapsule. Such disruption may be through mechanical means, chemical means, or a combination thereof. The disintegration can result, for example, from a change in pH; shearing; grinding; scrubbing (as with a brush or other implement); exposure to elevated temperatures; exposure to solvents such as water or saliva; and/or breakdown through enzymes. In certain exemplary embodiments, the disintegration results from a change in pH or primarily from a change in pH.

As disclosed herein, the pH-sensitive microcapsules comprise at least one functional ingredient. As used herein, "functional ingredient" refers to a material having a desired utility in the composition, such as a desired oral care, personal care, or home care utility. In various embodiments, such utilities may be therapeutic, cosmetic, aesthetic, decorative, cleansing, disinfecting, bleaching, whitening, descaling, sensory, or a combination thereof.

In certain compositions disclosed herein, the at least one functional ingredient may include, for example, flavorants, fragrances, essential oils, emulsifying agents, thickening agents, colorants, cooling agents, sweeteners, binding agents, sulfur precipitating agents, plasticizing agents, pharmaceutical actives, salivary stimulants, stain preventative agents, anti-microbial agents, anticaries agents, anticalculus agents, antiplaque agents, periodontal actives, breath freshening agents, malodor control agents, whitening agents, vitamins, herbs and herbal extracts, amino acids, enzymes or other proteins, steroids, anti-inflammatory agents, abrasives, antiperspirant actives, deodorant actives, conditioning agents, moisturizers, emollients, sunscreens, sunblocks, alcohols, denaturants, anti-dandruff agents, anticholinergics, anesthetics, foaming agents, surfactants, cleansing agents, bleaches, detergents, fabric softening agents, and preservatives. In various embodiments, the microcapsules may comprise at least one functional ingredient in an amount ranging from about 0.001% to about 50%, by weight of the microcapsule, such as about 0.01% to about 40%, about 0.1% to about 30%, about 1% to about 25%, or about 5% to about 15%, by weight of the microcapsule.

In various embodiments, the at least one functional ingredient may be a flavorant. In certain oral care embodiments, a flavorant may be rapidly released as the microcapsule disintegrates during use of the product, delivering a fresh breath flavor, desired mouthfeel, and/or sweetness into the oral cavity. Useful flavorants may include synthetic flavor oils or flavoring aromatics, oleo resins, and extracts derived from plants, leaves, flowers, fruits, and combinations thereof, as well as sweeteners. In certain embodiments, the microcapsule may comprise flavoring or food additives, such as those described in Chemicals Used in Food Processing, publication 1274 by the National Academy of Science, pages 63-258. In various embodiments, the microcapsule comprises at least one flavorant at a level ranging from about 0.01% to about 20%, about 0.1% to about 15%, about 1% to about 12%, or about 2% to about 10%, by weight relative to the weight of the microcapsule.

In certain embodiments, for example, flavor bloom and enhanced flavor perception occurs during contact with saliva and while brushing with a toothpaste, such as a toothpaste originally having an acidic pH, but achieving a neutralizing pH upon contact with the saliva.

In various embodiments, the microcapsule may comprise at least one functional ingredient that is a therapeutic active ingredient. As used herein, a "therapeutic active" is a material useful for the prevention or treatment of a physiological disorder or condition. Such disorders or conditions include those of the oral cavity (including teeth and gingiva), skin, hair, and eyes. The specific therapeutic active is preferably determined according to the desired utility of the composition. Such actives may include, for example, the following: antimicrobial agents, such as triclosan, cetyl pyridium chloride, domiphen bromide, quaternary ammonium salts, zinc compounds, sanguinarine, fluorides, alexidine, octonidine, and EDTA; essential oils; flavorants, such as thymol, methyl salicylate, eucalyptol, and menthol; non-steroidal anti-inflammatory drugs, such as aspirin, acetaminophen, ibuprofen, ketoprofen, diflunisal, fenoprofen calcium, naproxen, tolemetin sodium, and indomethacin; anti-tussives, such as benzonatate, caramiphen edisylate, menthol, dextromethorphan hydrobromide, and chlophendianol hydrochloride; decongestants, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine maleate, diphenhydramine citrate, doxylamine succinate, promethazine hydrochloride, pryilamine maleate, tripelannamine citrate, triprolidine hydrochloride, acrivastine, loratadine, brompheniramine, and dexbrompheniramine; expectorants, such as guaifenesin, ipecac, potassium iodide, and terpin hydrate; anti-diarrheas such as loperamide; $H_2$-antagonists such as famotidine and ranitidine; proton pump inhibitors, such as omeprazaole and lansoprazole; general nonselective CNS depressants, such as aliphatic alcohols and barbituates; general nonselective CNS stimulants such as caffeine, nicotine, strychnine, picrotoxin and pentylenetetrazol; drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, and bromide; antiparkinsonism drugs such as levodopa and amantadine; narcotic-analgesics, such as morphine, heroin, hydromorphone, metopon, oxymorphone, levorphanol, codeine, hydrocodone, oxycodone, nalorphine, naloxone, and naltrexone; analgesic-antipyretics such as salycilates, phenylbutazone, indomethacin, and phenacetin; and psychopharmacological drugs such as chlorpromazine, methotrimeprazine, haloperidol, clozapine, reserpine, imipramine, tranylcypromine, phenelzine, and lithium.

In certain embodiments, the microcapsules disclosed herein may include at least one fragrance compound as the functional ingredient. A wide variety of odiferous chemical compounds may be used as fragrances in the pH-sensitive microcapsule. Fragrance compounds include compounds used as perfumes and fragrances such as aldehydes, e.g., $C_6$-$C_{14}$ alipatic aldehydes and $C_6$-$C_{14}$ acyclic terpene aldehydes, ketones, alcohols, and esters. Suitable fragrance compounds include citral; neral; iso-citral; dihydro citral; citronellal; octanal; nonanal; decanal; undecanal; dodecanal; tridecanal; 2-methyl decanal; methyl nonyl acetaldehyde; 2-nonen-1-al; decanal; undecenal; undecylenic aldehyde; 2,6 dimethyl octanal; 2,6,10-trimethyl-9-undece-1-nal; trimethyl undecanal; dodecenal; melonal; 2-methyl octanal; 3,5,5, trimethyl hexanal and mixtures thereof. Fragrances may also include pro-fragrances such as acetal pro-fragrances, ketal pro-fragrances, ester pro-fragrances (e.g., digeranyl succinate), hydrolyzable inorganic-organic profragrances, and mixtures thereof. These pro-fragrances may release the perfume material as a result of simple hydrolysis. In certain embodiments disclosed herein, the microcapsule may comprise about 5% to about 40% fragrance, such as about 10% to about 25%, or, in certain embodiments, about 14% fragrance, based on the total weight of the microcapsule.

The pH-sensitive microcapsules disclosed herein may additionally include other ingredients, such as, a plasticizer, e.g., propylene glycol, surfactant, preservative, disintegration aid, and other ingredients.

The microcapsules disclosed herein may be incorporated in a carrier composition at a broad range of concentrations. In various embodiments, the carrier composition may comprise microcapsules in an amount of about 0.005% to about 15%, such as about 0.01% to about 12%, about 0.05 to about 10%, about 0.01 to about 8%, about 0.05 to about 5%, or about 0.5% to about 1%, by weight of the total composition.

As used herein, "carrier" refers to any material or composition in which a microcapsule can be embedded and suspended, and is suitable for administration or application to a subject, such as a human, an animal, clothing, and household surfaces. In various embodiments, the carrier has a pH that prevents or inhibits decomposition or dissolution of the microcapsules, such as a pH that is below about 6. In certain embodiments, the composition may be an oral care or personal care composition, or the composition may suitable for administration to a household surface, such as a home care composition. In certain embodiments, the carrier is a liquid, semi-solid, or solid. A liquid can be a liquid of low or high viscosity, and includes a liquid having a flowrate that is imperceptible under ambient conditions. For example, a soap, such as a bar of hand soap, can be considered a liquid as defined herein. A liquid can be a thixotropic liquid. A semi-solid, as used herein, can be a gel, a colloid, or a gum. As used herein, semi-solids and liquids are fluids that may be distinguished on the basis of viscosity: a semi-solid is a high viscosity fluid, while a liquid has a lower viscosity. There is no definitive dividing line between these two types of fluids. A semi-solid can, in certain embodiments, have a viscosity as high as thousands of mPas. Carrier compositions that may be mentioned include liquids, pastes, ointments, gels, and foams, and can be transparent, translucent, or opaque.

The specific composition of the carrier may depend on the intended use of the composition. In various embodiments, the carrier is aqueous, comprising about 5% to about 95% water, such as about 10% to about 80% water, or about 15% to about 75% water. In other embodiments, the carrier is substantially non-aqueous. In various embodiments, the carrier may be a dentifrice carrier having a water content of about 5% to about 70%, such as about 10% to about 50%, or about 200/% to about 400/%. In other embodiments, the non-aqueous dentifrice carrier comprises less than about 5% water.

The carrier may comprise any of a variety of materials, including emulsifiers, thickeners, fillers, and preservatives. In some embodiments, the carrier comprises at least one functional ingredient in addition to the functional ingredient that is encapsulated in the pH-sensitive microcapsules. The at least one functional ingredient may include, for example, any of those described above. In some embodiments, the carrier comprises the same functional ingredient as the microcapsules, and in certain embodiments the carrier comprises at least one different functional ingredient as the microcapsule.

In certain embodiments, the carrier is suitable for use as a dentifrice. In some embodiments, the carrier comprises a humectant, such as glycerine, sorbitol, or an alkylene glycol such as polyethylene glycol or propylene glycol. In certain embodiments, the carrier comprises a humectant at a level of about 10% to about 80% by weight relative to the weight of the carrier composition, such as about 20/o to about 60% by weight relative to the weight of the carrier composition.

In various compositions disclosed herein, the carrier comprises at least one of thickeners and gelling agents. Thickeners and gelling agents include, for example, inorganic, natural and synthetic thickeners and gelling agents. Examples of thickeners and gelling agents that may be used include inorganic thickening silicas such as amorphous silica, for example Zeodent® 165 (Huber Corporation); Irish moss; iota-carrageenan; gum tragacanth; or polyvinylpyrrolidone. In certain embodiments, the carrier comprises at least one polishing agent, such as silicas, calcined aluminas, sodium bicarbonate, calcium carbonate, dicalcium phosphate, and calcium pyrophosphate. In certain embodiments, the carrier can be a visually clear composition. In certain embodiments, the at least one gelling agent or thickener may be present in the carrier composition in an amount ranging from about 0.1% to about 15%, such as from about 0.4% to about 10%, by weight relative to the total weight of the carrier composition.

In certain compositions comprising a visually clear carrier composition, the composition may comprise at least one polishing agent. Polishing agents may include, for example, Zeodent® 115 (Huber Corporation), and alkali metal aluminosilicate complexes, such as a silica comprising alumina. In certain embodiments, a polishing agent can have a refractive index close to that of a gelling agent combined with water and/or humectant. In certain embodiments, the carrier composition comprises at least one polishing agent in an amount ranging from about 5% to about 70%, by weight relative to the total weight of the carrier composition.

In certain compositions, the carrier comprises at least one surfactant. Exemplary surfactants include water-soluble salts of at least one higher fatty acid monoglyceride monosulfate, such as the sodium salt of the monosulfated monoglyceride of hydrogenated coconut oil fatty acids; cocomidopropyl betaine; a higher alkyl sulfate such as sodium lauryl sulfate; an alkyl aryl sulfonate such as sodium dodecyl benzene sulfonate; a higher alkyl sulfonate; sodium lauryl sulfoacetate; a higher acid ester of 1,2-dihydroxy propane sulfonate; and substantially saturated higher aliphatic acyl amides of a lower aliphatic amino carboxylic acid, such as those having 12 to 16 carbons in the fatty acid, alkyl, or acyl radicals. Amides can be, for example, N-lauryl sarcosine, and the sodium, potassium, and ethanolamine salts of N-lauroyl, N-myristoyl, and N-palmitoyl sarcosine. In certain embodiments, the at least one surfactant may be present in the carrier composition in an amount ranging from about 0.3% to about 15%, such as about 0.5% to about 10%, or about 1% to about 3%, by weight relative to the total weigh of the carrier composition.

Also disclosed herein is the potential for longer-lasting release of functional ingredients, such as longer-lasting fresh breath and/or fragrance, wherein the pH-sensitive microcapsules may be optimized to comprise at least one functional ingredient at increasing encapsulation levels. For example, in one embodiment, a composition may comprise pH-sensitive microcapsules comprising at least one functional ingredient encapsulated within the shell wall in an amount of at least about 4%, such as at least about 10% or at least about 14%. In certain embodiments, compositions comprising increasing percentages of encapsulation of the at least one functional ingredient may demonstrate increased functionality, such as increased flavor or fragrance bloom.

The compositions disclosed herein may also, in certain embodiments, provide delayed release of at least one functional ingredient that is included in the pH-sensitive microcapsule. For example, when a fragrance compound is used as a functional ingredient, the fragrance may be released when the composition is used, i.e., when the composition comprising the pH-sensitive microcapsules contacts water, raising the pH of the solution to creating a bloom effect of fragrance at the time of use.

The delivery of functional ingredients such as fragrances into a composition includes evaluations of functional ingredient release and perception that can be measured quantitatively, qualitatively, objectively and/or subjectively, such as fragrance release, fragrance impact, fragrance longevity, user's perception of freshness and/or elimination or amelioration of malodor.

The pH-sensitive microcapsules disclosed herein may also add aesthetically desirable features to the composition, instead of or in addition to providing functional ingredients. The aesthetically desirable features may be visually distinguishable or visually indistinguishable from the carrier of compositions disclosed herein. In certain embodiments, the aesthetically desirable feature is a sensory contrast, which may be color contrast imparted by colorants such that the contrast is visually discernable. Desirable visual contrasts can be imparted by, for example, opacity, refractive index, reflective index, size, and shape. Colorants may be introduced into the microcapsule as a solid or as a color concentrate (e.g., a dye-containing, particulate polyethylene).

Any colorants well known in the art are suitable for use in the compositions disclosed herein. Formulation colorants among those useful herein include non-toxic water soluble dyes or pigments, such as, for example, metallic oxide "lakes." Suitable colorants may be approved for incorporation into a food or drug by a regulatory agency, such as FD&C or D&C pigments and dyes approved by the FDA for use in the United States. Suitable colorants also include a water insoluble inorganic pigment, such as titanium dioxide, chromium oxide green, phthalocyanine green, ultramarine blue, ferric oxide, metallic pigments such as aluminum flake pigments, pearlescent pigments such as pearlescent mica pigments, or a water insoluble dye flake. Suitable dye lakes include calcium or aluminum salts of an FD&C dye such as FD&C Green #1 lake, FD&C Blue #2 lake, D&C Red #30 lake or FD&C Yellow #15 lake. The microcapsules disclosed herein may comprise a dye such as D&C Red #30. A white colorant may also be used, including titanium dioxide, titanium dioxide coated mica (e.g., Timiron), a mineral, or a clay.

In various embodiments, the pH-sensitive microcapsules disclosed herein may exhibit other perceivable sensory contrast with the carrier. The perceivable sensory contrast can be, in additional to optical contrast, tactile contrast or olfactory contrast.

In certain embodiments, the compositions disclosed herein may include oral care compositions suitable for administration to the oral cavity. Such compositions include dentifrices (including mouthwashes and mouth rinses), dental gels, lozenges, beads, gums, oral strips, mints, liquid toothpastes, sprays, paint-on gels, lip balms, whitening strips, breath strips, oral chews, and dental flosses. An oral care composition disclosed herein can be used, for example, for cavity prevention, whitening, plaque prevention or reduction, gingivitis prevention or reduction, control of calculus, sensitivity prevention or reduction, breath malodor prevention or reduction, and stain prevention.

In certain embodiments, the compositions disclosed herein can be skin care compositions, for example, at least one of soaps, lotions, body washes, bath gels, shampoos, conditioners, deodorants, antiperspirants, fragrances, perfumes, and cosmetics.

In certain embodiments, the compositions disclosed herein can be home care compositions, for example dishwashing detergents, laundry detergents, fabric softeners, hard surface cleaners, and bleach compositions. Base compositions for home care compositions may include, for example, surfactants, detergents, and foaming agents.

The compositions as disclosed herein may also comprise one or more further agents typically selected from an flavorants, sweeteners, anti-plaque agent, a whitening agent, antibacterial agent, cleaning agent, adhesion agents, surfactants, foam modulators, abrasives, pH modifying agents, humectants, mouth feel agents, colorants, abrasive, tartar control (anticalculus) agent, fluoride ion source, saliva stimulating agent, nutrient and combinations thereof.

Flavorants among those useful herein include any material or mixture of materials operable to enhance the taste of the composition. Any orally acceptable natural or synthetic flavorant can be used, such as flavoring oils, flavoring aldhehydes, esters, alcohols and similar materials. Flavorants may, for example, include at least one of vanillin, sage, marjoram, parsley oil, spearmint oil, cinnamon oil, oil of wintergreen (methyl-salicylate), peppermint oil, clove oil, bay oil, anise oil, eucalyptus oil, citrus oil, fruit oils and essences including those derived from lemon, orange, lime, grapefruit, apricot, banana, grape, apple, strawberry, cherry, and pineapple; bean- and nut-derived flavors such as coffee, cocoa, cola, peanut, and almond; and adsorbed and encapsulated flavorants. Also encompassed within flavorants herein are ingredients that provide fragrance and/or other sensory effect in the mouth, including cooling or warming effects. Such ingredients may include at least one of menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), and methone glycerol acetal (MGA). In certain embodiments disclosed herein, the at least one flavorant is present in an amount ranging from about 0.01% to about 5%, such as about 0.05% to about 2%, from about 0.10% to about 2.5%, or from about 0.1% to about 0.5%, by weight relative to the weight of the total composition.

Sweetening agents among those useful herein include at least one of dextrose, polydextrose, sucrose, maltose, dextrin, dried invert sugar, mannose, xylose, ribose, fructose, levulose, galactose, corn syrup, partially hydrogenated starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, and dihydrochalcones.

The composition according to the present disclosure may comprise an antimicrobial agent which may be selected from halogenated diphenyl ether (triclosan); herbal extracts, essential oils and flavorants (e.g., rosemary extract, thymol, menthol, eucalyptol, methyl salicylate); bisguanide antiseptics (e.g., chlorhexidine, alexidine, or octenidine); phenolic antiseptics; hexetidine; povidone iodine; delmopinol; salifluor; sanguinarine; propolis; oxygenating agents (e.g., hydrogen peroxide, buffered sodium peroxyborate, or peroxycarbonate); cetyl pyridinium chloride; magnolia extract; magnolol; honokiol; butyl magnolol; propyl honokiol; and mixtures thereof. Anti-attachment agents such as Solrol also can be included, as well as plaque dispersing agents such as enzymes (papain, glucoamylase, etc.).

The compositions disclosed herein may further comprise an optional abrasive useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions disclosed herein may optionally comprise at least one fluoride ion source, which may be useful, for example, as an anti-caries agent. Any orally acceptable particulated fluoride ion source may be used, including potassium, sodium, and ammonium fluorides and monofluorophosphates, stannous fluoride, indium fluoride, and amine fluorides such as olaflur (N'-octadecyltrimethylenediamine-N,N,N'-tris(2-ethanol)-dihydrofluoride). The at least one fluoride ion source may be present in the oral care composition in an amount providing a clinically efficacious amount of soluble fluoride ion to the oral care composition.

In certain embodiments of the compositions disclosed herein, there may optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

Exemplary oral care compositions disclosed herein may comprise an orally acceptable carrier in a product such as a toothpaste or a gel. As used herein, "orally acceptable carrier" refers to a material or combination of materials that are safe for use in the oral care compositions disclosed herein, commensurate with a reasonable benefit/risk ratio.

Further disclosed herein is a method of making a composition comprising the pH-sensitive microcapsules disclosed herein. In certain embodiments, the pH-sensitive microcapsules disclosed herein may be made by preparing a shell wall fluid comprising at least one polymer chosen from hydroxypropyl methylcellulose derivatives and acrylate derivatives and at least one structuring agent chosen from shellac, ethyl cellulose, and fumed silica, and preparing a core fluid comprising at least one functional ingredient. To form or produce the microcapsules, the shell wall fluid and the core fluid may then be sprayed from a steady jet using a concentric nozzle comprising two chambers: an outer concentric shell fluid chamber and an inner core fluid chamber surrounded by the outer concentric shell fluid chamber.

In certain embodiments, the pH-sensitive microcapsule may be prepared using Flow Focusing® technology from Ingeniatrics, including, for example, a Flow Focusing® spray nozzle. The steady jet released from the nozzle comprises both shell fluid (from the outer concentric shell fluid chamber) and core fluid (from the inner core fluid chamber), and breaks up into droplets. The droplets may then be solidified, resulting in the formation of pH-sensitive microcapsules. The droplets may be solidified by any means known in the art, such as, for example, by thermal solvent evaporation/extraction, cooling, chemical hardening, and UV-curing. The pH-sensitive microcapsules may be added to a carrier composition having a pH of less than about 6, such as less than about 5.7, or less than about 5.5. The pH-sensitive microcapsules may be added to the carrier composition by any method known in the art and may, in certain embodiments, be suspended throughout the carrier composition. In certain embodiments, the pH-sensitive microcapsules may be suspended throughout the carrier composition relatively uniformly.

EXAMPLES

Example 1

A stannous fluoride toothpaste composition having a pH of 5.6 was obtained and used as a control. A second composition was prepared, comprising a base of the stannous fluoride toothpaste composition having a pH of 5.6 and 1% of microcapsule powder comprising Fancylemon COV2 fragrance. Samples prepared with the Fancylemon COV2 microcapsules were washed with hexane to remove fragrance from the surface of microcapsules. 0.5 grams of saliva or 0.5 grams of pH 7 buffer solution was added to 0.5 grams of the sample (i.e., a 1:1 ratio of saliva to sample or pH 7 buffer to sample). SPME analysis was conducted, and the resultant analytes were analyzed by gas chromatography/mass spectrometry to determine the headspace area count. The results are shown below in Table 1, illustrating an increase in the area counts for the fragrance after addition of either 0.5 grams of saliva or 0.5 grams of pH 7 buffer solution to 0.5 grams of the stannous fluoride sample comprising 1% Fancylemon fragrance. Accordingly, it was concluded that increased fragrance release occurred after the addition of both saliva and buffer (26% increase with saliva, 44% increase with pH 7 buffer). While not wishing to be bound by theory, the increase in area counts in the sample composition comprising 1% Fancylemon fragrance microcapsules is thought to be due to the presence of existing residual fragrance on the surface of the microcapsules.

TABLE 1

| SPME Analysis | |
|---|---|
| Composition | Count |
| Stannous fluoride base | 746,585.56 |
| Stannous fluoride base + 1% Fancylemon | 24,161,447.85 |
| Stannous fluoride base + 1% Fancylemon + saliva | 30,499,837.76 |
| Stannous fluoride base + 1% Fancylemon + pH 7 buffer | 34,786,618.66 |

A microcapsule leakage study was conducted to evaluated the stability of the microcapsules under aging conditions. Samples comprising stannous fluoride base toothpaste compositions having a pH of 5.6 plus 1% Fancylemon COV2 pH-sensitive microcapsules were aged both at room temperature and at 40° C. for 4 weeks, 8 weeks, and 13 weeks. SPME analysis was conducted on each sample, and the resultant analytes were analyzed by gas chromatography/mass spectrometry to determine the headspace area count. The results were compared to a sample composition comprising stannous fluoride base toothpaste having a pH of 5.6 plus 1% Fancylemon COV2 pH-sensitive microcapsules that had not been aged to determine a percent leakage of the aged samples. As shown below in Table 2, the results showed very minimal leakage, e.g., below 10%, indicating that the microcapsules were stable in the toothpaste composition.

TABLE 2

| Stability Study of Stannous Fluoride + 1% Fancylemon Toothpaste Samples | |
|---|---|
| Aging condition | % Microcapsule Leakage |
| 4 weeks at room temperature | 3.9 |
| 4 weeks at 40° C. | 6.8 |
| 8 weeks at room temperature | 4.5 |
| 8 weeks at 40° C. | 7.3 |
| 13 weeks at room temperature | 4.8 |
| 13 weeks at 40° C. | 4.6 |

Example 3

SPME analysis was conducted with 13-week aged stability samples to evaluate release of fragrance upon contact with saliva and with a pH 7 buffer. Samples of the stannous fluoride toothpaste composition comprising 1% Fancylemon fragrance microcapsules were contacted with saliva and pH 7 buffer. The analysis showed a 30% and 40% increase in headspace area counts for the samples aged for 13 weeks at room temperature when contacted with saliva and pH 7 buffer, respectively. The analysis further showed an 8% and 16% increase in headspace area counts for the samples aged for 13 weeks at 40° C. when contacted with saliva and pH 7 buffer, respectively. The data is shown below in Table 3.

TABLE 3

| SPME Analysis 13 Week Aged Samples of Stannous Fluoride Toothpaste with 1% Fancylemon COV2 Microcapsules | | |
|---|---|---|
| Composition | Room temperature | 40° C. |
| Stannous fluoride + 1% Fancylemon | 139,639,116.4 | 269,483,589.7 |
| Stannous fluoride + 1% Fancylemon + saliva | 182,104,252.6 | 291,824,321.0 |
| Stannous fluoride + 1% Fancylemon + pH 7 buffer | 196,136,689.9 | 338,133,616.2 |

Example 4

Several microcapsule compositions were prepared to encapsulate either a pine oil fragrance or Fancylemon COV2 fragrance. Table 4 below details the microcapsules prepared and the percent of encapsulated fragrance, based on the total weight of the microcapsule.

TABLE 4

Exemplary Microcapsules

| Compositions | Core Fragrance | Shell wall (ratio) | Shell wall thickness (μm) | % Entrapment |
|---|---|---|---|---|
| 1-13 | Fancylemon COV2 | Shellac:HPMCP:AMC7 (7:1:0.1) | ~12.7-~26.0 | 4.9-24.5 |
| 14-20 | Fancylemon COV2 | Shellac:HPMCP:HPC (7:1:0.1) | ~15.1-~23.7 | 5.4-29.9 |
| 21-28 | Fancylemon COV2 | Shellac:HPMCP:PVA (7:1:0.05) | ~15.0-~25.5 | 4.4-28.4 |
| 29-36 | Fancylemon COV2 | Shellac:HPMCP:PVA-PEG (7:1:0.1) | ~15.1-~26.9 | 4.9-19.4 |
| 37-40 | Fancylemon COV2 | Shellac:HPMCP (10:1) | ~13.7-~25.1 | 9.1-17.6 |
| 41-42 | Fancylemon COV2 | Shellac:HPMCP:AMC7 (10:1:0.05) | ~22.0-~25.3 | 9.5-14.8 |
| 43 | Fancylemon COV2 | Shellac:HPMCP:HPC (10:1:0.05) | ~21.5 | 11.7 |
| 44-45 | Pine oil | Shellac:HPMCP (10:1) | ~21.5 | 13.2 |
| 46-47 | Pine oil | Shellac:HPMCP:AMC7 (10:1:0.05) | ~21.5 | 14.0 |

HPMCP—hydroxypropyl methylcellulose phthalate
AMC7—anionic copolymer based on methacrylic acid and methyl methacrylate
HPC—hydroxypropyl cellulose
PVA—polyvinyl alcohol
PVA-PEG—polyvinyl alcohol polyethylene glycol

What is claimed is:

1. A composition comprising:
   at least one pH-sensitive microcapsule comprising (1) a shell wall comprising a polymer which is hydroxypropyl methyl cellulose phthalate, and a structuring agent which is shellac, wherein the weight ratio of the polymer and the structuring agent is at least about 1:7, and (2) at least one functional ingredient encapsulated inside the shell wall; and
   a carrier having a pH of less than about 6,
   wherein the at least one functional ingredient is released when the at least one microcapsule is contacted with a solution having a pH which is more basic than the carrier, wherein the shell wall further comprises at least one of anionic copolymers based on methacrylic acid and methyl methacrylate and
   wherein the at least one pH-sensitive microcapsule is incorporated in an oral care composition.

2. The composition according to claim 1, wherein the weight ratio of the at least one polymer and the at least one structuring agent is at least about 1:10.

3. The composition according to claim 1, wherein the at least one pH-sensitive microcapsule has a mean diameter ranging from about 25 μm to about 75 μm.

4. The composition according to claim 1, wherein the at least one pH-sensitive microcapsule has a mean diameter ranging from about 40 μm to about 50 μm.

5. The composition according to claim 1, wherein the shell wall has a thickness ranging from about 10 μm to about 30 μm.

6. The composition according to claim 1, wherein the shell wall has a thickness ranging from about 12 μm to about 26 μm.

7. The composition according to claim 1, wherein the at least one functional ingredient is chosen from flavorants, fragrances, essential oils, colorants, cooling agents, sweeteners, pharmaceutical actives, salivary stimulants, stain preventative agents, anti-microbial agents, anticaries agents, anticalculus agents, antiplaque agents, periodontal actives, breath-freshening agents, malodor control agents, whitening agents, vitamins, herbs and herbal extracts, amino acids, enzyme and other proteins, steroids, anti-inflammatory agents, anesthetics, cleansing agents, and bleaches.

8. The composition according to claim 1, wherein at least one functional ingredient is encapsulated inside the shell wall in an amount ranging from about 4% to about 30%, by weight based on the total weight of the at least one pH-sensitive microcapsule.

9. The composition according to claim 1, wherein the at least one polymer is present in the shell well in an amount ranging from about 5% to about 15% by weight based on the total weight of the at least one pH-sensitive microcapsule.

10. The composition according to claim 1, wherein the at least one structuring agent is present in the shell wall in an amount ranging from about 85% to about 95%, by weight based on the total weight of the at least one pH-sensitive microcapsule.

11. The composition according to claim 1, wherein the at least one functional ingredient remains encapsulated inside the shell wall for at least about 4 weeks when the composition is at room temperature.

* * * * *

UNITED STATES PATENT AND TRADEMARK OFFICE
CERTIFICATE OF CORRECTION

PATENT NO. : 11,166,889 B2
APPLICATION NO. : 15/756603
DATED : November 9, 2021
INVENTOR(S) : Evelyn Mohamed et al.

Page 1 of 1

It is certified that error appears in the above-identified patent and that said Letters Patent is hereby corrected as shown below:

In the Specification

Column 10, Line 31, delete "200% to about 400%." and insert -- 20% to about 40%. --, therefor.

Column 10, Line 51, delete "20/o" and insert -- 20% --, therefor.

Column 13, Line 25, delete "0.10%" and insert -- 0.1% --, therefor.

In the Claims

Column 18, Line 46, Claim 9, delete "well" and insert -- wall --, therefor.

Column 18, Line 47, Claim 9, delete "15%" and insert -- 15%, --, therefor.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*